(12) United States Patent
Wendland et al.

(10) Patent No.: US 10,702,651 B2
(45) Date of Patent: Jul. 7, 2020

(54) AUTO-INJECTOR

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 226 days.

(21) Appl. No.: 15/778,150

(22) PCT Filed: Nov. 21, 2016

(86) PCT No.: PCT/EP2016/078242
§ 371 (c)(1),
(2) Date: May 22, 2018

(87) PCT Pub. No.: WO2017/089254
PCT Pub. Date: Jun. 1, 2017

(65) Prior Publication Data
US 2018/0333537 A1    Nov. 22, 2018

(30) Foreign Application Priority Data
Nov. 27, 2015  (EP) .................................... 15196667

(51) Int. Cl.
*A61M 5/20* (2006.01)
*A61M 5/315* (2006.01)
*A61M 5/19* (2006.01)

(52) U.S. Cl.
CPC ...... *A61M 5/2033* (2013.01); *A61M 5/31505* (2013.01); *A61M 5/31515* (2013.01);
(Continued)

(58) Field of Classification Search
CPC ............ A61M 5/2033; A61M 5/31515; A61M 5/31505; A61M 5/31585; A61M 2205/8281
See application file for complete search history.

(56) References Cited

FOREIGN PATENT DOCUMENTS

WO  WO 2006/130100   12/2006
WO  WO 2008/083875    7/2008
(Continued)

OTHER PUBLICATIONS

International Search Report and Written Opinion in International Application No. PCT/EP2016/078242, dated Feb. 13, 2017, 10 pages.
(Continued)

*Primary Examiner* — Bradley J Osinski
(74) *Attorney, Agent, or Firm* — Fish & Richardson P.C.

(57) ABSTRACT

An auto-injector for delivering a liquid medicament comprising: a housing arranged to contain a syringe with a piston for sealing the syringe and displacing the medicament, the housing having a distal end and a proximal end intended to be applied against an injection site; a plunger unit arranged between the piston and the distal end of the housing, the plunger unit comprising a threaded internal surface for receiving and engaging a threaded rod element; and a tensioned elastic element fixed to the threaded rod element, the elastic element and the threaded rod element being fixed against rotation in an initial state, wherein when the elastic element is rotationally released, the threaded rod element rotates in a first direction, causing the plunger unit to translate towards the proximal end of the housing and thereby pushing the piston towards the proximal end of the housing to displace the medicament.

13 Claims, 3 Drawing Sheets

(52) U.S. Cl.
CPC ........... *A61M 5/31585* (2013.01); *A61M 5/19* (2013.01); *A61M 2205/8281* (2013.01)

(56) References Cited

FOREIGN PATENT DOCUMENTS

| WO | WO 2012/173553 | 12/2012 |
| WO | WO 2014/170267 | 10/2014 |
| WO | WO 2015/052221 | 4/2015 |
| WO | WO 2015/071123 | 5/2015 |

OTHER PUBLICATIONS

International Preliminary Report on Patentability in International Application No. PCT/EP2016/078242, dated May 29, 2018, 7 pages.

AUTO-INJECTOR

CROSS REFERENCE TO RELATED APPLICATIONS

The present application is the national stage entry of International Patent Application No. PCT/EP2016/078242, filed on Nov. 21, 2016, and claims priority to Application No. EP 15196667.8, filed in on Nov. 27, 2015, the disclosures of which are incorporated herein by reference.

TECHNICAL FIELD

The present disclosure relates to an auto-injector for delivering a liquid medicament to a user.

BACKGROUND

Current therapies delivered by means of self-administered injections include drugs for diabetes (both insulin and new GLP-A class drugs), migraine, hormone therapies, anticoagulants etc. Administering an injection is a process which presents a number of risks and challenges for user and healthcare professionals, both mental and physical.

Conventional injection devices typically fall under two categories—manual devices and auto-injectors. In a conventional manual device, a user must provide a force to drive a liquid medicament out of the device, e.g. by depressing a plunger. There are numerous disadvantages inherent with user of a manual device. For example, if the user stops depressing the plunger, less than a full dose of the liquid medicament may be delivered. Furthermore, the force required to depress the plunger may be problematic for elderly users or those with dexterity problems, which may lead to trembling or shaking when aligning or the injection and/or while administering the dose of the liquid medicament. In addition, the extension of the button or plunger of manual devices may be too great. Thus it can be inconvenient for the user to reach a fully extended button.

Auto-injectors aim to make self-administration of injected therapies easier for users. Auto-injectors are devices which completely or partially replace activities involved in medicament delivery of manual devices. These activities may include removal of a protective syringe cap, insertion of a needle into a patient's skin, injection of the medicament, removal of the needle, shield of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth.

In some auto-injectors plunger arrangements for provided for exerting a force to push the liquid medicament out of the syringe to be delivered to the user. These plunger arrangements are typically longitudinal in shape and take up a certain amount of space within the housing of the auto-injector. As such, there remains a need for an improved auto-injector with a plunger arrangement that allows the auto-injector to be more compact.

SUMMARY

According to an aspect of the present disclosure, there is provided an auto-injector for delivering a liquid medicament comprising: a housing arranged to contain a syringe with a piston for sealing the syringe and displacing the medicament, the housing having a distal end and a proximal end intended to be applied against an injection site; a plunger unit arranged between the piston and the distal end of the housing, the plunger unit comprising a threaded internal surface for receiving and engaging a threaded rod element; and a tensioned elastic element fixed to the threaded rod element, the elastic element and the threaded rod element being fixed against rotation in an initial state, wherein when the elastic element is rotationally released, the threaded rod element rotates in a first direction, causing the plunger unit to translate towards the proximal end of the housing and thereby pushing the piston towards the proximal end of the housing to displace the medicament.

The configuration of the plunger unit having a threaded internal surface for receiving and engaging the threaded rod element allows for a reduction in the overall length of the auto-injector. This provides the benefit for a more compact and portable auto-injector.

The elastic element may be a spiral spring coiled around the threaded rod element. The auto-injector may comprise a guide member for fixing the plunger unit against rotation. The guide member prevents the plunger unit from rotating due to the threaded inner surface configuration, therefore ensuring it only translates towards the proximal end of the housing.

The guide member may comprise a guide rib provided on a side wall of the housing arranged to engage with a protruding portion of the plunger unit.

The elastic element and the threaded rod element may be releasably fixed against rotation by a locking mechanism, and wherein when the locking mechanism is disengaged, the elastic element is rotationally released.

The locking mechanism may be provided at a first end of the threaded rod element.

The locking mechanism may comprise a first locking element provided at the threaded rod element and a second locking element, the first and second locking elements being configured to be releasably engaged with each other. This arrangement allows the locking mechanism to be easily actuated.

The second locking element may protrude out of the housing so as to allow manual operation of the locking mechanism.

The first locking element may be a groove provided at the first end of the threaded rod element, and the second locking element may be a movable projection, wherein when the projection is in a first position it is engaged with the groove and when the projection is in a second position it is disengaged from the groove. By using this mechanical arrangement, the plunger element can be released by simply moving the projection. This eliminates the need for an extending button for pushing a plunger and therefore prevents problems associated with users attempting to reach a fully extended button.

The first locking element may be a slot provided at the first end of the threaded rod element, and the second locking element may be a hook, wherein when the hook is in a first orientation it is engaged with the slot and when the hook is in a second orientation it is disengaged from the slot.

The second orientation may be achieved by rotating the rotatable cap from the first orientation.

A medicament may be included in the syringe.

According to another aspect of the present disclosure, there is provided a method of displacing a plunger unit in an auto-injector, the plunger unit comprising a threaded internal surface for receiving and engaging a threaded rod element, wherein upon release of a tensioned elastic element that is fixed to the threaded rod element, the threaded rod element rotates in a first direction, causing the plunger unit to displace in a lateral direction.

These and other aspects of the disclosure will be apparent from and elucidated with reference to the embodiments described hereinafter.

BRIEF DESCRIPTION OF THE DRAWINGS

Embodiments of the disclosure will now be described, by way of example only, with reference to the accompanying drawings, in which.

Reference will now be made in detail to the embodiments, examples of which are illustrated in the accompanying drawings, wherein like reference numerals refer to like elements throughout.

DETAILS DESCRIPTION OF THE EMBODIMENTS

An auto-injector with a plunger arrangement is provided. The plunger arrangement includes a plunger unit between a piston of a syringe and a distal end of a housing of the auto-injector, and a threaded rod element. Both the plunger unit and threaded rod element are provided with threaded surfaces, such that in an initial state the threaded rod element is received in an inner cavity of the plunger unit via the threaded arrangement.

The threaded rod element is fixedly attached to a tensioned spiral spring, which upon release would rotate in a first direction and causing the threaded rod element to also rotate in the first direction. By virtue of the threaded arrangement of the threaded rod element and the plunger unit, the plunger unit is caused to translate towards a proximal end of the housing and pushes the piston of the syringe for displacing liquid medicament contained in the syringe. The configuration of the auto-injector as described allows for increased compactness and portability.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml.

Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
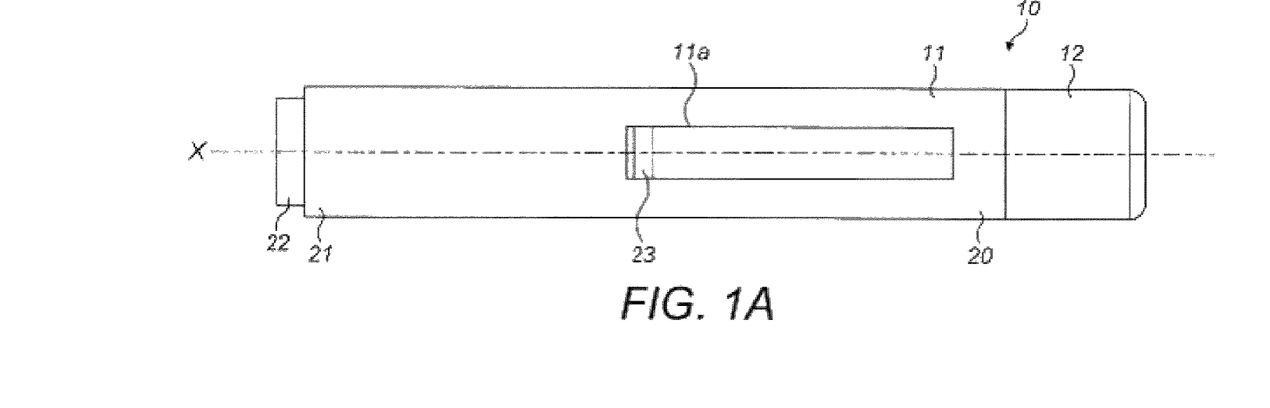
FIGS. 1A and 1B are side-on views of an auto-injector device according to an embodiment of the present disclosure.
Figure 1B:
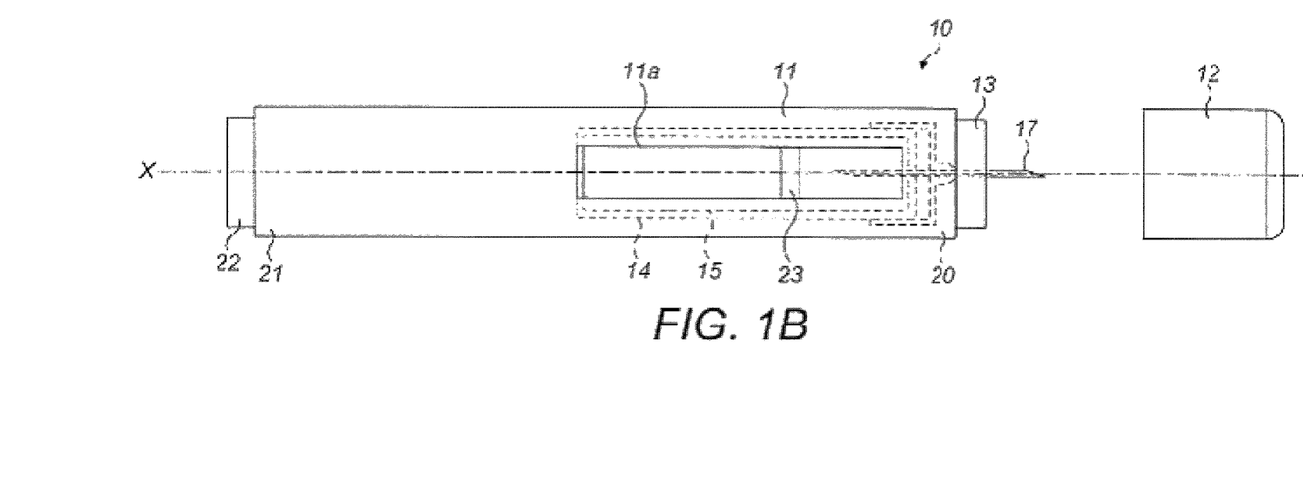

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2A:
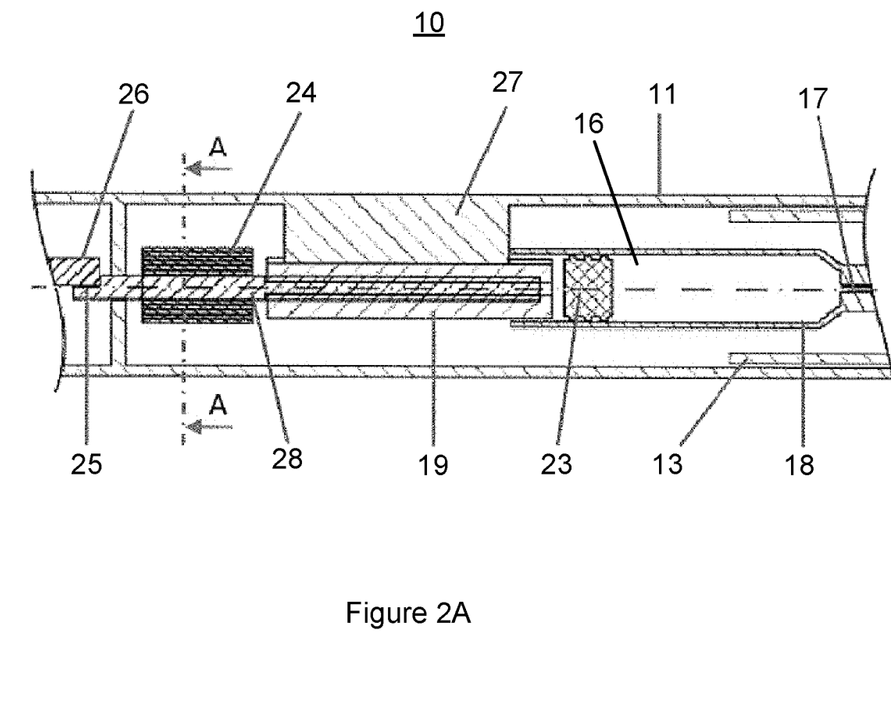
FIG. 2A is a cross-sectional view of an auto-injector device in an initial state, according to a first embodiment of the present disclosure.

FIG. 2A is a cross-sectional view of an auto-injector device 10 in an initial state, according to a first embodiment.

For illustrative purposes, FIG. 2A only shows a section of the auto-injector device 10. The auto-injector device 10 comprises a housing 11. The housing 11 is arranged to contain a syringe 18. The syringe 18 comprises a hollow injection needle 17 and a piston, stopper or bung 23 for sealing the syringe 18 and displacing liquid medicament 16 that is contained within the syringe 18. The housing 11 comprises a distal end and a proximal end intended to be applied against an injection site during injection of the liquid medicament 16.

A plunger unit 19 is arranged between the piston 23 and the distal end of the housing 11. The plunger unit 19 comprises a threaded internal surface for receiving and engaging a threaded rod element 28. The threaded rod element 28 is arranged between the plunger unit 19 and the distal end of the housing.

As shown in FIG. 2A, in the initial state the threaded rod element 28 is received at the plunger unit 19 such that it fills an inner cavity of the plunger unit 19. A tensioned elastic element 24 is fixed to the threaded rod element 28. The elastic element 24 is initially tensioned such that it has a tendency to rotate in a first direction. In the present embodiment, the elastic element 24 is a spiral spring coiled around the threaded rod element 28.

A first locking element 25 is provided at a first end of the threaded rod element 28 that is closer to the distal end of the housing 11. In the present embodiment, the first locking element is a groove 25 arranged at the first end of the threaded rod element 28. The first locking element is configured to be releasably engaged with a second locking element 26.

In the present embodiment, the second locking element 26 is a movable projection, and the groove 25 is releasably abutted by the projection 26 so as to hold the threaded rod element 28 and the tensioned spiral spring 24 against from rotation in the initial state. The groove 25 and movable projection 26 therefore form a locking mechanism for fixing the threaded rod element 28 and the spiral spring 24 against rotation in the initial state.

Figure 3A:
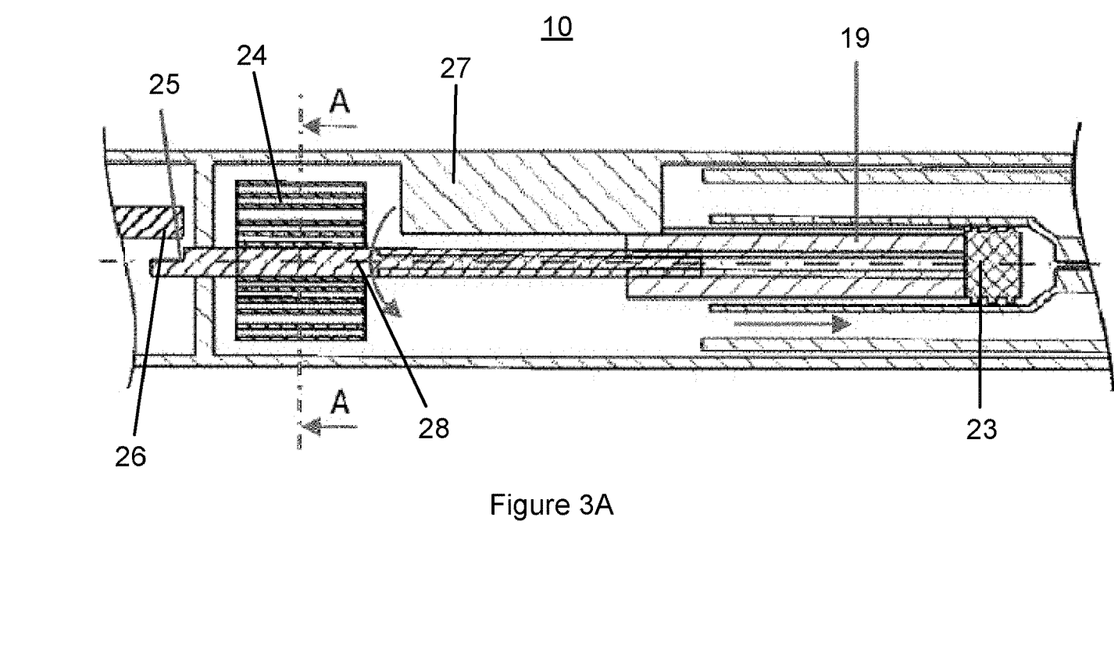
FIG. 3A is a cross-sectional view of the auto-injector device in a final state, according to the first embodiment of the present disclosure.

In the initial state as shown in FIG. 2A, the movable projection 26 is in a first position in which it is engaged with the groove 25. The movable projection 26 can be disengaged from the groove 25 by moving it from the first position to a second position, which is illustrated in FIG. 3A.

Although not shown in the drawing, in the present embodiment the movable projection protrudes out of the housing of the injector device 10 so as to allow manual operation. In other words, the user is able to move the projection 26 from the first position to the second position via the protruding second locking element 26.

A guide member 27 is provided on an inner surface of the housing 11 for fixing the plunger unit 19 against rotation. In the present embodiment, the guide member 27 comprises an elongated rib at a side wall of the housing 11 arranged to engage with a protruding portion of the plunger unit 19, as shown in FIG. 2A.

Figure 2B:
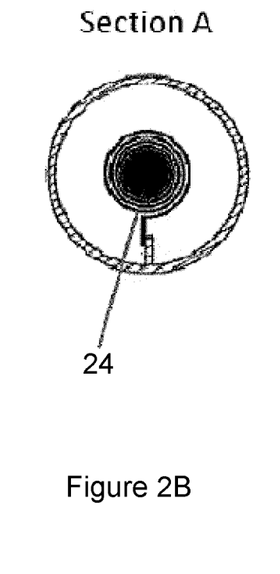
FIG. 2B is a cross-sectional view of the auto-injector device of FIG. 2A as taken along line A-A of FIG. 2A.

FIG. 2B is a cross-sectional view of the auto-injector device of FIG. 2A as taken along line A-A of FIG. 2A. FIG. 2B shows the housing 11 in a cylindrical shape containing within the tensioned spiral spring 24. In the initial state, the tensioned spiral spring 24 is coiled tightly and storing spring energy.

As will be described in further detail with respect to FIG. 3, the tensioned elastic element 24, i.e. spiral spring, is rotationally released when the locking mechanism (i.e. the groove 25 and the movable projection 26) is disengaged, causing the elastic element 24 to rotate in the first direction. The first direction in the present embodiment is the clockwise direction.

FIG. 3A is a cross-sectional view of the auto-injector device 10 in a final state, according to the first embodiment.

FIG. 3A shows a configuration of the auto-injector device 10 once the locking mechanism is disengaged, i.e. when the second locking element 26 disengages from the first locking element 25 of the threaded rod element 28, such that the threaded rod element 28 rotates under a driving force provided by the elastic element 24 being rotationally released.

In the present embodiment, the spiral spring 24 and the threaded rod element 28 are arranged to rotate in a first direction, i.e. clockwise. As the threaded rod element 28 rotates clockwise under the driving force from the spiral spring 24, the plunger unit 19 translates towards the proximal end of the housing due to the threaded engagement between the threaded rod element and the threaded internal surface of the plunger unit 19. The guide member 27 prevents the plunger unit 19 from rotating and therefore facilitates the translation of the plunger unit 19 in an axial direction towards the proximal end of the housing.

The rotation of the threaded rod inside the threaded internal surface of the plunger unit 19 causes the plunger unit 19 to translate towards the proximal end of the housing 11, thereby pushing the piston 23 and displacing the liquid medicament contained in the syringe 18 out of the injection needle 17. The auto-injector device 10 reaches the final state as the piston 23 reaches the end of the syringe 18 under the pushing force from the plunger unit 19, dispensing the liquid medicament in the syringe 18.

Figure 3B:
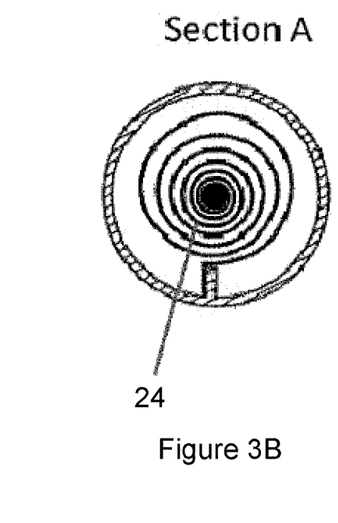
FIG. 3B is a cross-sectional view of the auto-injector device of FIG. 3A as taken along line A-A of FIG. 3A.

FIG. 3B is a cross-sectional view of the auto-injector device of FIG. 3A as taken along line A-A of FIG. 3A. In the final state, the spiral spring 24 is uncoiled and the stored spring energy has been released. Comparing FIGS. 2B and 3B, it can be seen that the elastic element 24 has been rotationally released in the clockwise direction (i.e. the first direction).

A sequence of operation of the auto-injector device 10 according to the first embodiment is as follows:

In the initial state, the threaded rod element 28 is received at the plunger unit 19 such that it fills an inner cavity of the plunger unit 19. The plunger unit 19 is fixed against rotation by the guide member 27, and the threaded rod element 28 along with the tensioned elastic element 24 are fixed against rotation by the locking mechanism.

In order to trigger an injection, the auto-injector device 10 is pressed against an injection site, e.g. a patient's skin. A user, e.g. the patient or a caregiver, grabs the auto-injector 10 device with their whole hand and pushes the proximal end of the auto-injector device 10 against the injection site.

When pushed against the injection site, the retractable sleeve of the auto-injector device 10 retracts into the housing 11 to expose the hollow injection needle 17, ready for injection. After the needle 17 has been inserted into the injection site, the projection 26 is manually operated such that it moves from the first position (as shown in FIG. 2A) to the second position (as shown in FIG. 3A). The projection 26 disengages from the groove 25 at the threaded rod element 28 and the threaded rod element 28 rotates under a driving force provided by the elastic element 24 being rotationally released.

As the threaded rod element 28 rotates clockwise under the driving force from the elastic element 24, the plunger unit 19 translates towards the proximal end of the housing 11 due to the threaded engagement between the threaded rod element and the threaded internal surface of the plunger unit 19.

The rotation of the threaded rod inside the threaded internal surface of the plunger unit 19 causes the plunger unit 19 to translate towards the proximal end of the housing 11, thereby pushing the piston 23 and displacing the liquid medicament contained in the syringe 18 out of the injection needle 17. The auto-injector device 10 reaches the final state as the piston 23 reaches the end of the syringe 18 under the pushing force from the plunger unit 19, dispensing the liquid medicament in the syringe 18 to the patient.

In alternative embodiments, instead of a rib, the guide member may be provided in another shape or form. For example, in an alternative embodiment, the guide member may be an appendage provided on the inner surface of the housing for fixing the plunger unit against rotation.

In alternative embodiments, an alternative elastic element may be provided instead of a spiral spring. For example, in such embodiments, a rubber band may be used as the elastic element.

In alternative embodiments, the locking mechanism may be provided at a different location at the auto-injector device, instead of at the first end of the threaded rod element. For example, the locking mechanism may be provided at side surface of the housing.

In alternative embodiments, the first and second locking elements may be provided in other configuration. For example, in such embodiments, the first locking element may be a slot arranged at the first end of the threaded rod element, while the second locking element is a hook. In this particular alternative embodiment, when the hook is in a first orientation it is engaged with the slot and when the hook is in a second orientation it is disengaged from the slot. Moreover, the second orientation may be achieved by rotating the hook from the first orientation.

Although claims have been formulated in this application to particular combinations of features, it should be understood that the scope of the disclosure also includes any novel features or any novel combinations of features disclosed herein either explicitly or implicitly or any generalisation thereof, whether or not it relates to the same disclosure as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Although a few embodiments have been shown and described, it would be appreciated by those skilled in the art that changes may be made in these embodiments without departing from the principles of the disclosure, the scope of which is defined in the claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta-'decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An auto-injector for delivering a liquid medicament comprising:
 a housing arranged to contain a syringe with a piston for sealing the syringe and displacing the medicament, the housing having a distal end and a proximal end intended to be applied against an injection site;
 a plunger unit arranged between the piston and the distal end of the housing, the plunger unit comprising a threaded internal surface for receiving and engaging a threaded rod element; and
 a tensioned elastic element fixed to the threaded rod element, the elastic element and the threaded rod element being fixed against rotation in an initial state,
 wherein when the elastic element is rotationally released, the threaded rod element rotates in a first direction, causing the plunger unit to translate towards the proximal end of the housing and thereby pushing the piston towards the proximal end of the housing to displace the medicament.

2. The auto-injector of claim 1, wherein the elastic element is a spiral spring coiled around the threaded rod element.

3. The auto-injector of claim 1, further comprising a guide member for fixing the plunger unit against rotation.

4. The auto-injector of claim 3, wherein the guide member comprises a guide rib provided on a side wall of the housing arranged to engage with a protruding portion of the plunger unit.

5. The auto-injector of claim 1, wherein the elastic element and the threaded rod element are releasably fixed against rotation by a locking mechanism, and wherein when the locking mechanism is disengaged, the elastic element is rotationally released.

6. The auto-injector of claim 5, wherein the locking mechanism is provided at a first end of the threaded rod element.

7. The auto-injector of claim 5, wherein the locking mechanism comprises a first locking element provided at the threaded rod element and a second locking element, the first and second locking elements being configured to be releasably engaged with each other.

8. The auto-injector of claim 7, wherein the second locking element protrudes out of the housing so as to allow manual operation of the locking mechanism.

9. The auto-injector of claim 7, wherein the first locking element is a groove provided at the first end of the threaded rod element, and the second locking element is a movable projection, wherein when the projection is in a first position it is engaged with the groove and when the projection is in a second position it is disengaged from the groove.

10. The auto-injector of claim 7, wherein the first locking element is a slot provided at the first end of the threaded rod element, and the second locking element is a hook, wherein when the hook is in a first orientation it is engaged with the slot and when the hook is in a second orientation it is disengaged from the slot.

11. The auto-injector of claim 10, wherein the second orientation is achieved by rotating a rotatable cap from the first orientation.

12. The auto-injector of claim 1, comprising a medicament included in the syringe.

13. A method of displacing a plunger unit in an auto-injector, the plunger unit comprising a threaded internal surface for receiving and engaging a threaded rod element, wherein upon release of a tensioned elastic element that is fixed to the threaded rod element, the threaded rod element rotates in a first direction, causing the plunger unit to displace in a lateral direction.

* * * * *

UNITED STATES PATENT AND TRADEMARK OFFICE
CERTIFICATE OF CORRECTION

PATENT NO. : 10,702,651 B2  
APPLICATION NO. : 15/778150  
DATED : July 7, 2020  
INVENTOR(S) : Stefan Wendland and Michael Harms

Page 1 of 1

It is certified that error appears in the above-identified patent and that said Letters Patent is hereby corrected as shown below:

In the Specification

In Column 1, Line 9 (approx.), delete "in on" and insert -- on --

Signed and Sealed this  
First Day of September, 2020

Andrei Iancu  
*Director of the United States Patent and Trademark Office*